United States Patent
Sharratt et al.

(10) Patent No.: US 8,367,879 B2
(45) Date of Patent: Feb. 5, 2013

(54) METHOD FOR THE PREPARATION OF 2 CHLORO 1,1,1,2,3,3,3 HEPTAFLUOROPROPANE

(75) Inventors: Andrew P. Sharratt, Cheshire (GB); John C. McCarthy, Warrington (GB)

(73) Assignee: Mexichem Amanco Holding S.A. de C.V. (MX)

( * ) Notice: Subject to any disclaimer, the term of this patent is extended or adjusted under 35 U.S.C. 154(b) by 57 days.

(21) Appl. No.: 12/734,517

(22) PCT Filed: Nov. 10, 2008

(86) PCT No.: PCT/GB2008/003775
§ 371 (c)(1),
(2), (4) Date: Aug. 16, 2010

(87) PCT Pub. No.: WO2009/060221
PCT Pub. Date: May 14, 2009

(65) Prior Publication Data
US 2010/0312026 A1    Dec. 9, 2010

(30) Foreign Application Priority Data
Nov. 9, 2007   (GB) .................................. 0721991.8

(51) Int. Cl.
*C07C 17/20*   (2006.01)
(52) U.S. Cl. ..................................................... 570/170
(58) Field of Classification Search .................. 570/170
See application file for complete search history.

(56) References Cited

U.S. PATENT DOCUMENTS

| | | | |
|---|---|---|---|
| 5,043,491 A | 8/1991 | Webster et al. | |
| 5,057,634 A | 10/1991 | Webster et al. | |
| 2001/0011061 A1 | 8/2001 | Scott et al. | |
| 2003/0105368 A1 | 6/2003 | Iikubo et al. | |
| 2004/0127757 A1 | 7/2004 | Iikubo et al. | |
| 2006/0217578 A1 | 9/2006 | Rao et al. | |
| 2007/0123742 A1 | 5/2007 | Rao et al. | |
| 2008/0207964 A1 | 8/2008 | Rao et al. | |

FOREIGN PATENT DOCUMENTS

| | | |
|---|---|---|
| CA | 1162511 | 2/1984 |
| CA | 2081813 | 1/2004 |
| DE | 3017154 | 12/1981 |
| EP | 434408 | 6/1991 |
| EP | 434409 | 6/1991 |
| EP | 539989 | 5/1993 |
| EP | 666105 | 8/1995 |
| EP | 502605 | 7/1996 |
| EP | 1350564 | 10/2003 |
| WO | 99/51553 | 10/1999 |
| WO | 99/51556 | 10/1999 |
| WO | 03/029173 | 4/2003 |
| WO | 2004/018397 | 3/2004 |
| WO | 2005/037742 | 4/2005 |
| WO | 2005/037744 | 4/2005 |
| WO | 2007/019354 | 2/2007 |
| WO | 2007/019356 | 2/2007 |

*Primary Examiner* — Jafar Parsa
(74) *Attorney, Agent, or Firm* — Ryan Kromholz & Manion, S.C.

(57) ABSTRACT

A method of catalytically converting 2,2, dichlorohexafluoropropane (HFC-216aa) into 2 chloro 1,1,1,2,3,3,3 heptafluoropropane (HFC-217ba) including the step of exposing the 2,2 dichlorohexafluoropropane to a chromium-containing catalyst comprising a metal oxide, a halogenated metal oxide or a metal oxyhalide, which chromium-containing catalyst comprises 0.01% to 5.0% by weight zinc or a compound of zinc.

16 Claims, No Drawings

METHOD FOR THE PREPARATION OF 2 CHLORO 1,1,1,2,3,3,3 HEPTAFLUOROPROPANE

This invention relates to a preparation method for preparing 2 chloro 1,1,1,2,3,3,3 heptafluoropropane (HFC-217ba) from 2,2 dichlorohexafluoropropane (HFC-216aa).

HFC-216aa is a known haloalkane. It may have particularly industrial suitability as a known precursor of hexafluoropropene, into which it is readily converted by known reactions, for example by catalytic hydrodehalogeneration, for example at elevated temperature in the presence of hydrogen. Hexafluoropropene is itself a useful compound, and has a variety of uses including as a co-polymer in the production of fluoroethylene polymer, and as a precursor to HFC-227ea and to hexafluoropropylene oxide, and thence to hexafuoroacetone and sevoflurane. In addition, it can readily be converted by known processes into 1,2,3,3,3 pentafluoropropene (HFC-1225ye), which itself has potential use in refrigerant blends, in particular for use in automobile air conditioning.

It is known from U.S. Pat. No. 5,057,634 (DuPont de Nemours) that HFC-216aa can be catalytically converted into HFC-217ba at elevated temperature by a large number of catalysts, including a variety of chromia catalysts.

In addition, U.S. Pat. No. 5,043,491 (DuPont de Nemours) describes a multi-step synthesis of hexafluoropropylene from propane, which describes a number of suitable catalysts, including chromia catalysts for chlorofluorination of propane and/or propylene, and for the hydrodehalogenation of the resultant halopropane.

The listing or discussion of an apparently prior-published document in this specification should not necessarily be taken as an acknowledgement that the document is part of the state of the art or is common general knowledge.

We have found a process whereby HFC-216aa can be catalytically converted into HFC-217ba using a particular catalyst which provides particularly satisfactory results, in particular in terms of selectivity of the process, and also the ability to operate the process at a lower operating temperature, thereby resulting in potential cost savings.

Thus, according to a first aspect of the invention, there is provided a method of catalytically converting 2,2, dichlorohexafluoropropane (HFC-216aa) into 2 chloro 1,1,1,2,3,3,3 heptafluoropropane (HFC-217ba) including the step of exposing the 2,2 dichlorohexafluoropropane to a chromium containing catalyst comprising a metal oxide, a halogenated metal oxide or a metal oxyhalide, which chromium-containing catalyst comprises 0.01% to 5.0% by weight zinc or a compound of zinc.

The process is conveniently carried out in the presence of HF. The process is preferably carried out in the vapour phase.

The catalyst used in the process of the invention is generally described in EP-A-666105 (Imperial Chemical Industries plc), the contents of which are hereby incorporated by reference.

A key to the present invention lies in carefully controlling the amount of zinc or zinc-containing compound in the chromium-containing catalyst. Conveniently, the level of zinc used in the chromium-containing catalyst is such as to act as an activity promoter in the conversion of HFC-216aa to HFC-217ba.

Preferably, the chromium-containing catalyst contains chromium in the form of chromia, halogenated chromia or chromium oxyfluoride. Alternatively the chromium-containing catalyst may contain chromium itself. Typically however, so during operation of the catalyst in the fluorination process in which it is employed, or during a prefluorination treatment of the catalyst as hereinafter described, chromium in whatever form in the initial catalyst is converted to chromia, halogenated chromia or chromium oxyfluoride.

Furthermore, the chromium-containing catalyst may also comprise metal oxides, halogenated metal oxides or metal oxyfluorides other than chromia, halogenated chromia or chromium oxyfluoride, which may be present in addition to, or instead of chromia, halogenated chromia or chromium oxyfluoride. The metal oxide may be for example alumina, magnesia or zirconia, and in particular magnesia and alumina, which during operation of the catalyst may be converted at least in part to aluminium fluoride and magnesium fluoride respectively. Thus, the chromium-containing catalyst may also comprise metal fluorides, for example aluminium fluoride and magnesium fluoride.

Thus, the chromium-containing catalyst may comprise an amount of zinc or a compound of zinc in and/or on a support such as a mixed metal oxide support, for example chromia/magnesia or a compound of zinc in and/or on a metal oxide support which also comprises chromium, for example, zinc on chromium-containing alumina or magnesia. In the latter case the chromium may be converted to chromia, halogenated chromia or chromium oxyfluoride during operation of the process employing the catalyst. Further, the chromium-containing catalyst may comprise an amount of zinc in and/or on a mixed metal oxide/fluoride support, for example alumina/chromium fluoride or chromia/magnesium fluoride; or an amount of zinc on a metal fluoride, for example chromium fluoride, magnesium fluoride or aluminium fluoride, or mixed metal fluoride support, for example chromium fluoride/aluminium fluoride or chromium fluoride/magnesium fluoride, providing that in all these cases, the catalyst comprises chromium in one form or another.

Moreover, the chromium-containing catalyst may comprise an activated carbon support.

The amount of zinc present in the catalyst is important, since the introduction of too much zinc may result in sub-optimal results. However, the use of very low levels of zinc can be shown to provide benefits over the inclusion of no zinc at all. The zinc content of the catalyst is preferably 0.01% to 5.0%, and is preferably at least 0.1% by weight of the catalyst. In certain preferred embodiments, the zinc is present at a level of at least 0.5% by weight of the catalyst It is to be understood that the amounts of zinc given herein refer to the amount of zinc, whether present as elemental zinc or as a compound of zinc, but that where the zinc is present as a compound of zinc, the amount refers only to the amount of zinc, and not the amount of compound of zinc.

The zinc may be introduced into and/or onto the catalyst in the form of a compound, for example a halide, oxyhalide, oxide or hydroxide depending at least to some extent upon the catalyst preparation technique employed. In the case where catalyst preparation is by impregnation of a chromia, halogenated chromia or chromium oxyhalide, the compound is preferably a water-soluble salt, for example a halide, nitrate or carbonate, and is employed as an aqueous solution or slurry. Alternatively, the hydroxides of the promoter and chromium may be co-precipitated and then converted to the oxides to prepare the catalysts, for example a catalyst comprising a mixed oxide or zinc and chromium. Mixing and milling of an insoluble zinc compound with the basic catalyst provides a further method of preparing the catalyst. A method for making catalysts based on chromium oxyhalide comprises adding a compound of the promoter to hydrated chromium halide and calcining the mixture.

Further methods for preparing the catalyst include, for example, reduction of a chromium (VI) compound, for example a chromate, dichromate, in particular ammonium dichromate, to chromium (III), by zinc metal, followed by co-precipitation, washing and calcining; or mixing a solids, a chromium (VI) compound and an oxidisable zinc compound, for example zinc acetate or zinc oxalate, and heating the mixture to high temperature in order to effect reduction of the chromium (VI) compound to chromium (III) oxide and the zinc salt to zinc oxide.

Any of the aforementioned methods, or other methods may be employed for the preparation of the chromium-containing zinc promoted catalysts of the present invention.

The amount of zinc introduced to the catalyst depends upon the catalyst preparation employed. It is believed that the working catalyst has a surface containing the zinc cations located in a chromium-containing catalyst, for example chromium oxide, oxyhalide, or halide lattice and it is the amount of such surface zinc which determines the activity of the catalyst. Thus the amount of the zinc which is required may be lower for catalysts made by impregnation than for catalysts made by other methods and containing the promoter in non-surface locations The zinc/chromia catalysts used in the present invention may be amorphous. By this we mean that the catalyst does not demonstrate substantial crystalline characteristics when analysed by, for example, X-ray diffraction.

Alternatively, the catalysts may be partially crystalline. By this we mean that from 0.1 to 50% by weight of the catalyst is in the form of one or more crystalline compounds of chromium and/or one or more crystalline compounds of zinc. If a partially crystalline catalyst is used, it preferably contains from 0.2 to 25% by weight, more preferably from 0.3 to 10% by weight, still more preferably from 0.4 to 5% by weight of the catalyst in the form of one or more crystalline compounds of chromium and/or one or more crystalline compounds of zinc.

During use in a dehydrohalogenation reaction the degree of crystallinity may change. Thus it is possible that a catalyst of the invention that has a degree of crystallinity as defined above before use in a dehydrohalogenation reaction and will have a degree of crystallinity outside these ranges during or after use in a dehydrohalogenation reaction.

The percentage of crystalline material in the catalysts of the invention can be determined by any suitable method known in the art. Suitable methods include X-ray diffraction (XRD) techniques. When X-ray diffraction is used the amount of crystalline material such as the amount of crystalline chromium oxide can be determined with reference to a known amount of graphite present in the catalyst (e.g. the graphite used in producing catalyst pellets) or more preferably by comparison of the intensity of the XRD patterns of the sample materials with reference materials prepared from suitable internationally recognised standards, for example NIST (National Institute of Standards and Technology) reference materials.

The catalysts of the invention typically have a surface area of at least 50 m$^2$/g, preferably from 70 to 250 m$^2$/g and most preferably from 100 to 250 m$^2$/g before it is subjected to pre-treatment with a fluoride containing species such as hydrogen fluoride or a fluorinated hydrocarbon. During this pre-treatment, at least some of the oxygen atoms in the catalyst are replaced by fluorine atoms.

The fluorination catalyst will usually be subjected to a prefluorination treatment with hydrogen fluoride, and optionally an inert diluent, prior to use in the catalysis of fluorination reactions. A typical pre-treatment comprises heating the catalyst at 250° C. to 450° C. in contact with hydrogen fluoride, preferably a mixture of hydrogen fluoride and nitrogen or pure hydrogen fluoride. The working catalyst may consequently comprise at least part zinc fluoride in and/or on a fluorinated chromium-containing catalyst, for example fluorinated chromia or chromium oxyfluoride.

The catalyst may be in the form of pellets or granules of appropriate size for use in a fixed bed or a fluidised bed. It may be regenerated or reactivated periodically by heating in air at a temperature of from about 300° C. to about 500° C. Air may be used as a mixture with an inert gas such as nitrogen or with hydrogen fluoride which emerges hot from the catalyst treatment process, and may be used directly in fluorination processes employing the reactivated catalyst.

If desired, the catalyst may contain one or more metals other than zinc, for example nickel or cobalt, or it may contain for example other divalent metals, although we generally prefer that the catalyst does not comprise other metals such as nickel, cobalt or other divalent metals.

The fluorination conditions employed may be those known to be useable when employing chromium-containing catalysts, for example atmospheric or superatmospheric pressure, hydrogen fluoride and temperatures in the range of 180° C. to about 500° C. depending upon the particular fluorination reaction being carried out.

The use of the catalysts outlined herein in the process of the invention allows the process to be carried out at a relatively low temperature compared to those with different catalysts; alternatively if the same process temperature is used, a shorter contact time is required using the described catalysts.

The process of the invention may be part of a multi-stage process; for example it may be the second stage of a more general method outlined below:

$$C_3H_6 + Cl_2 \text{ (excess)} + HF\text{(excess)} \rightarrow CF_3CCl_2CF_3 \quad (a)$$

$$CF_3CCl_2CF_3 + HF \rightarrow CF_3CClFCF_3 \quad (b)$$

$$CF_3CClFCF_3 + H_2 \rightarrow CF_3CF{=}CF_2 \quad (c)$$

The resultant $CF_3CF{=}CF_2$ has a number of possible utilities, but may in a preferred embodiment be hydrogenated to produce $CF_3CHFCHF_2$, and subsequently dehydrofluorinated to provide 1,2,3,3,3 pentafluoropropene (HFC-1225ye).

At least a stoichiometric amount of hydrogen fluoride is usually used in the preferred process of the invention. Topical amounts include from 1 to 10 moles, conveniently 1 to 6 moles of hydrogen fluoride per mole of HFC-216aa. Accordingly, the products of the reaction will usually contain unreacted hydrogen fluoride in addition to HFC-217ba and by-products.

Conveniently, the process is carried out at a temperature of 350° C. to 500° C., preferably 400° C. to 460° C.

Preferably, the process is carried out at a pressure of 0.1 to 30 barg, preferably 5 to 25 barg, conveniently 10 to 20 barg.

Preferably, the process is carried out for a reaction time of 1 second to 60 minutes, preferably 1 second to 10 minutes, preferably 10 seconds to 5 minutes.

The reaction and any separation steps utilized which make up the invention may be performed using conventional equipment and techniques.

It is preferred that the process according to the invention be operated continuously. In practice however, catalyst deactivation, necessitating periodic catalyst regeneration or reactivation, may interrupt continuous operation of the process.

The feeding of air to the catalyst during operation of the process may counter catalyst deactivation and reduce the frequency of process interruption for catalyst regeneration or reactivation.

The use of the process of the invention has been found in the production of HFC-217ba to produce a 20° C. or more benefit in operating temperature, and improved selectivity. In addition, it was beneficially found that most of the by-products produced could be recycled, thereby making selectivity (although beneficial) not crucial.

EXAMPLES

Example 1

Various catalyst samples of differing formulation were tested. After charging (2-6 g), the catalyst was dried (250° C. for 1 hour) and pre-fluorinated ($N_2$:HF of 6 for 1 hour at 250° C., the temperature was ramped to 380° C., the nitrogen diluent was switched off and left overnight). A commercially pre-fluorinated catalyst sample was also tested. In this case, the catalyst was only subjected to the drying stage of the pre-fluorination process prior to use. Following pre-fluorination, the reactor was cooled and the feed flows (HF and HFC-216aa) established and set. Both feeds were delivered by sparging liquid with nitrogen. When stable, the feeds were diverted to the reactor and a temperature scan experiment performed. Off-gas samples were taken at each temperature and analysed by GC and GC-MS.

The results are shown in Table 1.

In the first two experiments a 5.2% Zn/chromia prepared by co-precipitation and pre-fluorinated in situ was compared to a commercially pre-fluorinated pure chromia. Just 2 g of catalyst was used for these experiments and so the contact times were relatively low. Significant conversion of HFC-216aa to HFC-217ba was not observed until 400° C. Thereafter, conversion increased with temperature, but the performance of both catalysts appeared very similar, indicating that Zn was not acting as a promoter. Analysis of the reactor off-gases by GC-MS identified the following by-products:

HFC-115 (chloropentafluoro ethane), hexafluoropropylene, HFC-1215's, and chlorofluoropropenes including HFC-1214 and HFC-1213.

With the exception of HFC-115, all of these compounds are readily recycleable.

From the results it can be seen the two low Zn-containing catalysts (0.137% zinc, and 0.537% zinc) were markedly better than catalysts comprising neat chromia (i.e. no zinc), the catalyst comprising 5.2% zinc/chromia. With the two low zinc catalysts, it was possible to achieve approximately 40% conversion of HFC-216aa at 400° C. instead of 420° C., and with improved selectivity (70-80%, instead of approximately 65%).

TABLE 1

| Catalyst Type | Charge (g) | HF feed (ml/min) | 216aa flow (ml/min) | Temperature (° C.) | Contact time (S) | Conversion (%) | Selectivity (%) |
|---|---|---|---|---|---|---|---|
| 5.2% Zn | 2 | 6.4 | 1.5 | 360 | 6.0 | 1.4 | 59.0 |
|  |  | 6.4 | 1.5 | 380 | 5.8 | 2.1 | 81.9 |
|  |  | 6.4 | 1.5 | 400 | 5.6 | 4.1 | 82.6 |
|  |  | 6.4 | 1.5 | 420 | 5.4 | 10.1 | 74.9 |
|  |  | 6.4 | 1.5 | 440 | 5.3 | 19.1 | 68.8 |
|  |  | 6.4 | 1.5 | 460 | 5.1 | 20.0 | 82.7 |
|  |  | 6.4 | 1.5 | 460 | 5.1 | 19.7 | 85.4 |
| 0% Zn (Commerically Pre-fluorinated) | 2 | 8.5 | 1.5 | 250 | 5.7 | 0.8 | 3.2 |
|  |  | 8.5 | 1.5 | 300 | 5.2 | 0.8 | 6.0 |
|  |  | 8.5 | 1.5 | 400 | 4.4 | 5.9 | 89.8 |
|  |  | 8.5 | 1.5 | 420 | 4.3 | 12.7 | 90.3 |
|  |  | 8.5 | 1.5 | 420 | 4.3 | 12.1 | 89.9 |
|  |  | 8.5 | 1.5 | 440 | 4.2 | 19.2 | 90.0 |
|  |  | 8.5 | 1.5 | 460 | 4.1 | 28.0 | 89.3 |
|  | 6 | 8.5 | 1.5 | 300 | 15.6 | 0.9 | 8.2 |
|  |  | 8.5 | 1.5 | 360 | 14.1 | 2.1 | 30.0 |
|  |  | 8.5 | 1.5 | 380 | 13.7 | 5.0 | 26.6 |
|  |  | 8.5 | 1.5 | 400 | 13.3 | 16.6 | 52.8 |
|  |  | 8.5 | 1.5 | 420 | 12.9 | 40.0 | 64.3 |
|  |  | 8.5 | 1.5 | 440 | 12.5 | 63.0 | 60.7 |
|  |  | 8.5 | 1.5 | 460 | 12.2 | 69.2 | 87.1 |
| 0.137% Zn | 6 | 8.6 | 1.5 | 340 | 14.4 | 1.3 | 52.4 |
|  |  | 8.6 | 1.5 | 360 | 14.0 | 2.7 | 66.3 |
|  |  | 8.6 | 1.5 | 380 | 13.5 | 21.7 | 71.1 |
|  |  | 8.6 | 1.5 | 400 | 13.1 | 37.9 | 71.0 |
|  |  | 8.6 | 1.5 | 420 | 12.8 | 56.2 | 65.5 |
|  |  | 8.6 | 1.5 | 440 | 12.4 | 69.8 | 74.2 |
|  |  | 8.6 | 1.5 | 460 | 12.1 | 79.8 | 69.4 |
|  |  | 8.6 | 1.5 | 360 | 14.0 | 2.3 | 83.6 |
|  |  | 8.6 | 1.5 | 380 | 13.5 | 5.9 | 83.7 |
|  |  | 8.6 | 1.5 | 400 | 13.1 | 39.5 | 81.4 |
|  |  | 8.6 | 1.5 | 420 | 12.8 | 68.7 | 77.2 |
|  |  | 8.6 | 1.5 | 440 | 12.4 | 82.4 | 70.0 |
|  |  | 8.6 | 1.5 | 460 | 12.1 | 79.2 | 79.8 |
| 0% Zn | 6 | 10 | 1.5 | 340 | 12.7 | 1.1 | 67.7 |
|  |  | 10 | 1.5 | 360 | 12.3 | 1.5 | 74.6 |
|  |  | 10 | 1.5 | 380 | 11.9 | 0.7 | 27.8 |
|  |  | 10 | 1.5 | 400 | 11.5 | 2.3 | 86.4 |
|  |  | 10 | 1.5 | 420 | 11.2 | 45.7 | 88.8 |
|  |  | 10 | 1.5 | 440 | 10.9 | 71.0 | 79.7 |
|  |  | 10 | 1.5 | 460 | 10.6 | 84.0 | 63.2 |

The invention claimed is:

1. A method of catalytically converting 2,2, dichlorohexafluoropropane (HFC-216aa) into 2 chloro 1,1,1,2,3,3,3 heptafluoropropane (HFC-217ba) including the step of exposing the 2,2 dichlorohexafluoropropane to a chromium-containing catalyst comprising a metal oxide, a halogenated metal oxide or a metal oxyhalide, which chromium-containing catalyst comprises 0.01% to 5.0% by weight zinc or a compound of zinc.

2. A method according to claim 1, wherein the process is carried out in the presence of HF.

3. A method according to claim 2, wherein the process is carried out in the vapour phase.

4. A method according to claim 1, wherein chromium containing catalyst contains chromium in the form of chromia, halogenated chromia or chromium oxyfluoride.

5. A method according to claim 1, wherein the chromium-containing catalyst comprises a support.

6. A method according to claim 1, wherein the level of zinc in the catalyst is at least 0.1% by weight of the catalyst.

7. A method according to claim 6, wherein the level of zinc in the catalyst is at least 0.5% by weight of the catalyst.

8. A method according to claim 1, wherein the catalyst is amorphous.

9. A method according to claim 1, wherein the catalyst is partially crystalline.

10. A method according to claim 1, wherein the catalyst has a surface area in the range 70 to 250 m2/g.

11. A method according to claim 1, wherein the catalyst is pre-fluorinated prior to the reaction.

12. A method according to claim 1, wherein the reaction is carried out at a temperature of 350 to 500° C.

13. A method according to claim 12, wherein the reaction is carried out at a temperature of 400 to 460° C.

14. A method according to claim 1, wherein the reaction is carried out at a pressure of 0.1 to 30 barg.

15. A method according to claim 1, wherein the reaction is carried out for a period of 1 second to sixty minutes.

16. A method according to claim 1, wherein the reaction is carried out continuously.

* * * * *

UNITED STATES PATENT AND TRADEMARK OFFICE
CERTIFICATE OF CORRECTION

PATENT NO. : 8,367,879 B2  Page 1 of 1
APPLICATION NO. : 12/734517
DATED : February 5, 2013
INVENTOR(S) : Sharratt et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 155 days.

Signed and Sealed this
First Day of September, 2015

Michelle K. Lee
*Director of the United States Patent and Trademark Office*